(12) United States Patent
Hoefer et al.

(10) Patent No.: US 7,674,934 B2
(45) Date of Patent: Mar. 9, 2010

(54) STABILIZERS FOR USE IN NVP SYNTHESIS

(75) Inventors: Frank Hoefer, Bad Duerkheim (DE); Alexandra Brand, Darmstadt (DE); Arnd Boettcher, Kuantan (MY); Katrin Baumann, Mannheim (DE); Regina Vogelsang, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 296 days.

(21) Appl. No.: 11/659,331

(22) PCT Filed: Aug. 4, 2005

(86) PCT No.: PCT/EP2005/008466

§ 371 (c)(1),
(2), (4) Date: May 9, 2007

(87) PCT Pub. No.: WO2006/015799

PCT Pub. Date: Feb. 16, 2006

(65) Prior Publication Data

US 2008/0312432 A1    Dec. 18, 2008

(30) Foreign Application Priority Data

Aug. 5, 2004   (DE) .................. 10 2004 038 109

(51) Int. Cl.
| | |
|---|---|
| C07C 231/12 | (2006.01) |
| C07D 233/58 | (2006.01) |
| C07D 207/12 | (2006.01) |
| C07D 211/02 | (2006.01) |
| C07D 201/02 | (2006.01) |

(52) U.S. Cl. ............... 564/215; 548/335.1; 548/543; 548/552; 546/185; 546/243; 540/533; 540/534; 540/538

(58) Field of Classification Search ............. None
See application file for complete search history.

(56) References Cited

U.S. PATENT DOCUMENTS

| | | | |
|---|---|---|---|
| 2,317,804 A | 4/1943 | Reppe et al. | |
| 4,410,726 A | 10/1983 | Parthasarathy et al. | |
| 5,665,889 A * | 9/1997 | Chu et al. | .......... 548/543 |
| 2002/0002280 A1 | 1/2002 | Bottcher et al. | |

FOREIGN PATENT DOCUMENTS

| | | |
|---|---|---|
| DE | 1 176 124 | 6/1962 |
| DE | 199 62 138 | 6/2001 |
| EP | 0 646 571 | 4/1995 |
| GB | 573 752 | 12/1945 |
| WO | 00 39085 | 7/2000 |

* cited by examiner

*Primary Examiner*—Brian J Davis
(74) *Attorney, Agent, or Firm*—Oblon, Spivak, McClelland, Maier & Neustadt, L.L.P.

(57) ABSTRACT

A process for preparing N-alkenyl compounds by reacting the corresponding NH compounds with alkynes in the liquid phase in the presence of a catalyst, wherein the reaction is carried out in the presence of at least one stabilizer, and the use of stabilizers for increasing the selectivity in a process for preparing N-alkenyl compounds by reacting the corresponding NH compounds with alkynes in the liquid phase in the presence of a catalyst.

17 Claims, No Drawings

STABILIZERS FOR USE IN NVP SYNTHESIS

The present invention relates to a process for preparing N-alkenyl compounds by reacting the corresponding NH compounds with alkynes in the liquid phase in the presence of a catalyst, and to the use of stabilizers in a process for preparing N-alkenyl compounds.

N-Alkenylamides are used as monomers in the production of plastics and coatings. Polyvinylamides serve, for example, as laundry detergents, as assistants in cosmetic and medicinal products, and for the stabilization and clarifying filtration of beers and fruit juices. Polyvinyllactams, especially polyvinylpyrrolidone, have broad application and serve, for example, as dispersants for pigments, as laundry detergents, as assistants in cosmetic and medicinal products, and assistants in textile processing and adhesive technology.

In the vinylation processes for preparing N-alkenylamides, relatively large amounts of polymers are obtained. In the prior art, attempts are made to minimize this amount of polymers by various processes.

WO 00/39085 describes a one-stage reaction for preparing N-vinylpyrrolidone or N-vinylcaprolactam from acetylene and the corresponding nitrogen compound. To increase the reaction rate and the selectivity, the process is carried out at a high concentration of acetylene in the nonaqueous reaction solution. The high concentration of acetylene in the reaction solution is achieved by carrying out the reaction at low temperatures and high pressures.

EP-A 0 646 571 discloses a process for preparing N-vinyl compounds by reacting the corresponding amines with acetylene in the presence of compounds of the group of the platinum group metals as catalysts.

DE-A 1 176 124 describes a process for preparing N-vinylamides in which acetylene is reacted with N-amides in the liquid phase in the presence of a basic catalyst. The N-vinylamide formed is removed very rapidly from the reaction zone after it has been formed.

DE-A 199 62 138 discloses a process for preparing N-alkenylamides by reacting the corresponding NH amides with alkynes in the liquid phase in the presence of basic alkali metal compounds and diols as cocatalysts.

The prior art has described the use of stabilizers hitherto only in the storage, transport and purification of N-alkenyl compounds, but not in the preparation of N-alkenyl compounds.

It is an object of the present invention to provide a process for preparing N-alkenyl compounds, wherein the formation of polymers is reduced, or prevented.

The achievement of the object starts from a process for preparing N-alkenyl compounds by reacting the corresponding NH compounds with alkynes in the liquid phase in the presence of a catalyst.

The process according to the invention comprises carrying out the reaction in the presence of at least one stabilizer.

The process according to the invention is notable for high conversions even at low reaction temperatures, low catalyst concentration and low concentration of the alkyne used. It is not necessary to use a cocatalyst. In addition, it has been found that, surprisingly, the inventive use of stabilizers allows the selectivity of the reaction to be improved.

In the process according to the invention, preference is given to reacting alkynes of the general formula I and NH compounds of the general formula II in the presence of a catalyst and of at least one stabilizer to give N-alkenyl compounds of the general formula III

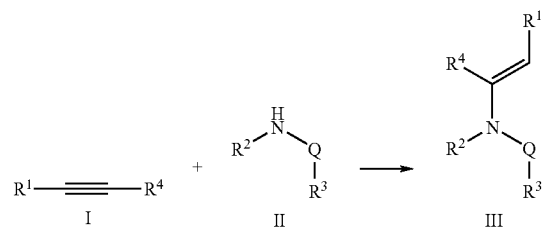

where Q, $R^1$, $R^2$, $R^3$ and $R^4$ are each defined in accordance with the invention as follows:

Q is C=O or $CR^1$ $R^1$, $R^4$ are each independently hydrogen, $C_1$-$C_{20}$-alkyl, $C_2$-$C_{20}$-alkenyl, $C_2$-$C_{20}$-alkynyl, $C_3$-$C_{10}$-cycloalkyl, $C_7$-$C_{18}$-aralkyl, $C_6$-$C_{18}$-aryl or $C_5$-$C_{18}$-heteroaryl, where the radicals mentioned may optionally be substituted by functional groups and/or one or more nonadjacent carbon atoms of the alkyl, alkenyl, alkynyl or cycloalkyl radicals may be replaced by heteroatoms, preferably N, S or O.

$R^2$, $R^3$ are each independently hydrogen, $C_1$-$C_{20}$-alkyl, $C_2$-$C_{20}$-alkenyl, $C_2$-$C_{20}$-alkynyl, $C_3$-$C_{10}$-cycloalkyl, $C_7$-$C_{18}$-aralkyl, $C_6$-$C_{18}$-Aryl or $C_5$-$C_{18}$-heteroaryl, where the radicals mentioned may optionally be substituted by functional groups and/or one or more nonadjacent carbon atoms of the alkyl, alkenyl, alkynyl or cycloalkyl radicals may be replaced by heteroatoms, preferably N, S or O, and one of the $R^2$ or $R^3$ radicals has to be different to hydrogen.

The $R^2$—N-Q-$R^3$ moiety may also be part of a saturated, unsaturated or aromatic, heterocyclic four- to eight-membered ring which optionally contains up to two further heteroatoms, preferably selected from the group consisting of N, O and S, and may optionally be substituted by functional groups and optionally additionally be fused.

The four- to eight-membered ring containing the $R^2$—N-Q-$R^3$ moiety may additionally or exclusively be substituted by one or more radicals selected from the group consisting of $C_1$-$C_{20}$-alkyl, $C_2$-$C_{20}$-alkenyl, $C_2$-$C_{20}$-alkynyl, $C_3$-$C_{10}$-cycloalkyl, $C_7$-$C_{18}$-aralkyl $C_6$-$C_{18}$-aryl and/or $C_5$-$C_{18}$-heteroaryl, where the radicals mentioned may optionally be substituted by functional groups and/or one or more nonadjacent carbon atoms of the alkyl, alkenyl, alkynyl or cycloalkyl radicals may be replaced by heteroatoms, preferably N, O or S.

Suitable functional groups are, for example, hydroxyl, aldehyde, keto, amino, amido, imido, imino, ether, thioether, carboxyl groups and derivatives thereof, and halogens, phosphines and phosphites, preferably phosphines and phosphites.

Alkynes in the process according to the invention are all organic compounds which correspond to the general formula I, i.e. have at least one triple bond.

The $R^1$, $R^2$, $R^3$ and $R^4$ radicals may each independently be $C_1$-$C_{20}$-alkyl, preferably $C_1$-$C_8$-alkyl, for example methyl, ethyl, n-propyl, isopropyl, n-butyl, isobutyl, sec-butyl, tert-butyl.

In addition, $R^1$, $R^2$, $R^3$ and $R^4$ may each independently be $C_2$-$C_{20}$-alkenyl, preferably $C_2$-$C_8$-alkenyl, for example ethenyl, propenyl or butenyl.

Moreover, $R^1$, $R^2$, $R^3$ and $R^4$ may each independently be $C_2$-$C_{20}$-alkynyl, preferably $C_2$-$C_{10}$-alkynyl, for example butynyl, pentynyl, hexynyl.

$R^1$, $R^2$, $R^3$ and $R^4$ may moreover each independently be $C_3$-$C_{10}$-cycloalkyl, preferably $C_3$-$C_6$-cycloalkyl, for example cyclopropyl, cyclobutyl, cyclopentyl, cyclohexyl, cycloheptyl.

$R^1$, $R^2$, $R^3$ and $R^4$ may in addition each independently be $C_7$-$C_{18}$-aralkyl, preferably $C_7$-$C_{12}$-aralkyl, for example benzyl.

Moreover, $R^1$, $R^2$, $R^3$ and $R^4$ may each independently be $C_6$-$C_{18}$-aryl, preferably $C_6$-$C_{15}$-aryl, for example phenyl, naphthyl.

In addition, $R^1$, $R^2$, $R^3$ and $R^4$ may each independently be $C_5$-$C_{18}$-heteroaryl, preferably $C_5$-$C_{10}$-heteroaryl, for example pyridinyl, pyrimidinyl, imidazyl, benzotriazyl, furyl, thiophenyl, pyryl, phenyl, quinaldyl, naphthyl.

The above-listed alkyl, alkenyl, alkynyl, cycloalkyl, aralkyl, aryl and heteroaryl groups may be substituted as mentioned above, or one or more carbon atoms of the alkyl, alkenyl, alkynyl or cycloalkyl groups may be replaced by heteroatoms as mentioned above.

$R^1$, $R^2$, $R^3$ and $R^4$ are preferably each independently hydrogen, $C_1$-$C_8$-alkyl, $C_2$-$C_8$-alkenyl.

In a further preferred embodiment, $R^2$ and $R^3$ together with the N-Q moiety form a saturated, unsaturated or aromatic, four- to eight-membered, preferably five- to seven-membered ring which optionally contains up to two further heteroatoms, preferably selected from N, O or S, is optionally substituted by functional groups and is optionally fused, preferably benzofused. In addition, the ring may bear one or more radicals selected from $C_1$-$C_{20}$-alkyl, $C_2$-$C_{20}$-alkenyl, $C_2$-$C_{20}$-alkynyl, $C_3$-$C_{10}$-cycloalkyl, $C_7$-$C_{18}$-aralkyl, $C_6$-$C_{18}$-aryl and/or $C_5$-$C_{18}$-heteroaryl, and the radicals mentioned may optionally be substituted by functional groups and/or one or more nonadjacent carbon atoms of the alkyl, alkenyl, alkynyl or cycloalkyl radicals may be replaced by heteroatoms, preferably N, O or S.

Particular preference is given to Q, $R^1$, $R^2$, $R^3$ and $R^4$ each being defined as follows:

Q is C=O or $CR^1$, $R^1$, $R^4$ are each independently hydrogen, $C_1$-$C_8$-alkyl, $C_2$-$C_8$-alkenyl, $R^2$, $R^3$ are each independently hydrogen, $C_1$-$C_8$-alkyl, $C_2$-$C_8$-alkenyl, or the $R^2$—N-Q-$R^3$ moiety is part of a saturated or unsaturated, heterocyclic four- to eight-membered ring which optionally contains N as a further heteroatom, and which may optionally be substituted by $C_1$-$C_8$-alkyl, $C_2$-$C_8$-alkenyl, $C_2$-$C_8$-alkynyl, $C_3$-$C_6$-cycloalkyl and/or $C_6$-$C_{10}$-aryl, when Q is C=O or CH.

Very particular preference is given to Q, $R^1$, $R^2$, $R^3$ and $R^4$ each being defined as follows:

Q is C=O or $CR^1$, $R^1$, $R^4$ are each hydrogen, $R^2$, $R^3$ are each hydrogen, or $R^2$ and $R^3$ together with the N-Q moiety, when Q is C=O, form a five-, six- or seven-membered ring which does not have any further heteroatoms or any further substituents, or, when Q is CH, form an unsaturated five-membered containing N as a heteroatom and not having any further substituents.

Very particular preference is thus given to using acetylene as the alkyne of the general formula I.

Very particularly preferred compounds of the general formula II are 2-pyrrolidone, 2-piperidone, ε-caprolactam, formamide and imidazole.

Very particular preference is thus given to using the process according to the invention for reacting acetylene with 2-pyrrolidone to give N-vinyl-2-pyrrolidone (N-vinyl-γ-butyrolactam), acetylene with 2-piperidone to give N-vinyl-2-piperidone (N-vinyl-δ-valerolactam), acetylene with ε-caprolactam to give N-vinyl-ε-caprolactam, acetylene with formamide to give N-vinylformamide, or acetylene with imidazole to give N-vinylimidazole.

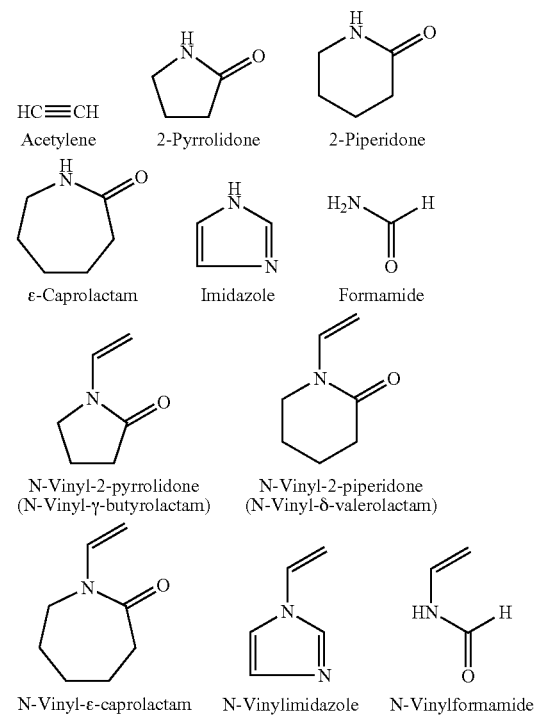

The process according to the invention is carried out in the presence of a catalyst, and the catalyst used is a compound selected from the group consisting of alkali metals, alkali metal compounds, alkaline earth metal compounds, rare earth metal compounds and compounds of the metals of the platinum group or mixtures thereof.

Preference is given to using alkali metal compounds or alkaline earth metal compounds as catalysts in the process according to the invention. The catalysts used are more preferably basic alkali metal compounds or basic alkaline earth metal compounds.

The basic alkali metal compounds used in the process according to the invention may be the hydrides, oxides, hydroxides and/or alkoxides of lithium, sodium, potassium, rubidium, cesium, calcium, barium and/or strontium, and mixtures thereof. The alkoxides used are preferably the compounds of low molecular weight alcohols, for example methoxide, ethoxide, propoxide, 1-methylethoxide, butoxide, 1-methylpropoxide, 2-methylpropoxide and 1,1-dimethylethoxide. Preference is given to using the hydrides, oxides, hydroxides and/or alkoxides of sodium and/or potassium.

The catalyst used in the process according to the invention is more preferably sodium hydroxide, potassium hydroxide and potassium hydride or mixtures thereof.

The basic alkali metal compounds may be used in the form of solids or solutions in water or alcohol. Preference is given to using solid, anhydrous and alcohol-free alkali metal compounds.

The catalyst in the process according to the invention is present generally in a molar proportion of from 0.01 to 10 mol %, based on the molar amount of the NH compound used, preferably from 0.02 to 6.0 mol %, and more preferably from 0.05 to 4.0 mol %.

In addition, the process according to the invention is carried out in the presence of at least one stabilizer.

Stabilizers refer generally to compounds which suppress the spontaneous and thus undesired polymerization in the course of the processing and storage of monomers. Stabilizers are thus delimited by definition from other reaction additives. While the former prevent product losses as a result of undesired side reactions, suitable reaction additives are intended to influence properties of the reaction mixture. In particular, a better process is desired, for example better mixing, more rapid reaction of the reactants or the like.

It has been found that the inventive use of stabilizers in the process according to the invention for preparing N-alkenyl compounds of the general formula III from alkynes of the general formula I and NH compounds of the general formula II improves the selectivity both based on the NH compound used and on the alkyne used in comparison to prior art processes.

The stabilizer used in the process according to the invention may be at least one compound selected from the group consisting of phenols, quinones, hydroquinones, N-oxyls, aromatic amines, phenylenediamines, hydroxylamines, urea derivatives, phosphorus compounds, sulfur compounds, metal salts, complexing agents and mixtures of two or more of these compounds.

Experience has shown that the introduction of such stabilizers leads to full or partial hydrolysis or full or partial protonation. Products which are protonated in the appropriate media or are present fully or partly as the hydrolyzed compound or in equilibrium likewise form part of the subject-matter of the invention.

Phenols may, for example, phenol, o-, m- or p-cresol (methylphenol), 2-tert-butyl-4-methyl-phenol, 6-tert-butyl-2,4-dimethylphenol, 2,6-di-tert-butyl-4-methylphenol, 2-tert-butyl-phenol, 4-tert-butylphenol, 2,4-di-tert-butylphenol, 2-methyl-4-tert-butylphenol, 4-tert-butyl-2,6-dimethylphenol, or 2,2'-methylenebis(6-tert-butyl-4-methylphenol), 4,4'-oxy-diphenyl, 3,4-(methylenedioxy)diphenol (sesamol), 3,4-dimethylphenol, hydroquinone, pyrocatechol (1,2-dihydroxybenzene), 2-(1'-methylcyclohex-1'-yl)-4,6-dimethylphenol, 2- or 4-(1'-phenyleth-1'-yl)phenol, 2-tert-butyl-6-methylphenol, 2,4,6-tris-tert-butylphenol, 2,6-di-tert-butylphenol, 2,4-di-tert-butylphenol, 4-tert-butylphenol, nonylphenol [11066-49-2], octylphenol [140-66-9], 2,6-dimethylphenol, bisphenol A, bisphenol F, bisphenol B, bisphenol C, bisphenol S, 3,3',5,5'-tetrabromobisphenol A, 2,6-di-tert-butyl-p-cresol, Koresin® from BASF AG, methyl 3,5-di-tert-butyl-4-hydroxybenzoate, 4-tert-butylpyrocatechol, 2-hydroxybenzyl alcohol, 2-methoxy-4-methylphenol, 2,3,6-trimethylphenol, 2,4,5-trimethylphenol, 2,4,6-trimethylphenol, 2-isopropylphenol, 4-iso-propylphenol, 6-isopropyl-m-cresol, n-octadecyl β-(3,5-di-tert-butyl-4-hydroxyphenyl)-propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1,3,5-tris(3,5-di-tert-butyl-4-hydroxybenzyl) isocyanurate, 1,3,5-tris(3,5-di-tert-butyl-4-hydroxyphenyl)propionyl-oxyethyl isocyanurate, 1,3,5-tris(2,6-dimethyl-3-hydroxy-4-tert-butylbenzyl) isocyanurate or pentaerythrityl tetrakis[β-(3,5-di-tert-butyl-4-hydroxyphenyl)propionate], 2,6-di-tert-butyl-4-dimethylaminomethylphenol, 6-sec-butyl-2,4-dinitrophenol, Irganox® 565, 1141, 1192, 1222 and 1425 from Ciba Spezialitätenchemie, octadecyl 3-(3',5'-di-tert-butyl-4'-hydroxyphenyl)propionate, hexadecyl 3-(3',5'-di-tert-butyl-4'-hydroxyphenyl)propionate, octyl 3-(3',5'-di-tert-butyl-4'-hydroxyphenyl)propionate, 3-thia-1,5-pentanediyl bis[(3',5'-di-tert-butyl-4'-hydroxyphenyl)propionate], 4,8-dioxa-1,11-undecanediyl bis[(3',5'-di-tert-butyl-4'-hydroxyphenyl) propionate], 4,8-dioxa-1,11-undecanediyl bis[(3'-tert-butyl-4'-hydroxy-5'-methylphenyl)propionate], 1,9-nonanediyl bis [(3',5'-di-tert-butyl-4'-hydroxyphenyl)-propionate], 1,7-heptanediamine bis[3-(3',5'-di-tert-butyl-4'-hydroxyphenyl)-propionamide], 1,1-methanediamine bis [3-(3',5'-di-tert-butyl-4'-hydroxyphenyl)-propionamide], 3-(3',5'-di-tert-butyl-4'-hydroxyphenyl)propanohydrazide, 3-(3',5'-dimethyl-4'-hydroxyphenyl)propanohydrazide, bis(3-tert-butyl-5-ethyl-2-hydroxyphen-1-yl)methane, bis(3,5-di-tert-butyl-4-hydroxyphen-1-yl)methane, bis[3-(1'-methylcyclohex-1'-yl)-5-methyl-2-hydroxyphen-1-yl]methane, bis(3-tert-butyl-2-hydroxy-5-methylphen-1-yl)methane, 1,1-bis (5-tert-butyl-4-hydroxy-2-methylphen-1-yl)ethane, bis(5-tert-butyl-4-hydroxy-2-methylphen-1-yl) sulfide, bis(3-tert-butyl-2-hydroxy-5-methylphen-1-yl) sulfide, 1,1-bis(3,4-dimethyl-2-hydroxyphen-1-yl)-2-methylpropane, 1,1-bis(5-tert-butyl-3-methyl-2-hydroxyphen-1-yl)butane, 1,3,5-tris-[1'-(3'',5''-di-tert-butyl-4''-hydroxyphen-1''-yl)meth-1'yl]-2,4,6-trimethylbenzene, 1,1,4-tris(5'-tert-butyl-4'-hydroxy-2'-methylphen-1'-yl)butane, aminophenols, for example para-aminophenol, nitrosophenols, for example para-nitrosophenol, p-nitroso-o-cresol, alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, 3,5-di-tert-butyl-4-hydroxyanisole, 3-hydroxy-4-methoxybenzyl alcohol, 2,5-dimethoxy-4-hydroxybenzyl alcohol (syringa alcohol), 4-hydroxy-3-methoxybenzaldehyde (vanillin), 4-hydroxy-3-ethoxybenzaldehyde (ethylvanillin), 3-hydroxy-4-methoxybenzaldehyde (isovanillin), 1-(4-hydroxy-3-methoxyphenyl)-ethanone (acetovanillone), eugenol, dihydroeugenol, isoeugenol, or tocopherols, for example α-, β-, γ-, δ- and ε-tocopherol, tocol, α-tocopherolhydroquinone, and also 2,3-dihydro-2,2-dimethyl-7-hydroxybenzofuran (2,2-dimethyl-7-hydroxycoumaran), Trolox®, gallic acid, ferulic acid, cinnamic acid and derivatives thereof.

Quinones and hydroquinones may, for example, be hydroquinone or hydroquinone methyl ether, 2,5-di-tert-butylhydroquinone, 2-methyl-p-hydroquinone, 2,3-dimethylhydroquinone, trimethylhydroquinone, 4-methylpyrocatechol, tert-butylhydroquinone, 3-methylpyrocatechol, benzoquinone, 2-methyl-p-hydroquinone, 2,3-dimethylhydroquinone, trimethylhydroquinone, 3-methylpyrocatechol, 4-methylpyrocatechol, tert-butylhydroquinone, 4-ethoxyphenol, 4-butoxyphenol, hydroquinone monobenzyl ether, p-phenoxyphenol, 2-methylhydroquinone, 2,5-di-tert-butyl-hydroquinone, tetramethyl-p-benzoquinone, diethyl 1,4-cyclohexanedione-2,5-dicarboxylate, phenyl-p-benzoquinone, 2,5-dimethyl-3-benzyl-p-benzoquinone, 2-isopropyl-5-methyl-p-benzoquinone (thymoquinone), 2,6-diisopropyl-p-benzoquinone, 2,5-dimethyl-3-hydroxy-p-benzoquinone, 2,5-dihydroxy-p-benzoquinone, embelin, tetrahydroxy-p-benzoquinone, 2,5-dimethoxy-1,4-benzoquinone, 2-amino-5-methyl-p-benzoquinone, 2,5-bisphenylamino-1,4-benzoquinone, 5,8-dihydroxy-1,4-naphthoquinone, 2-anilino-1,4-naphthoquinone, anthraquinone, N,N-dimethylindoaniline, N,N-diphenyl-p-benzoquinonediimine, 1,4-benzoquinone dioxime, coerulignone, 3,3'-di-tert-butyl-5,5'-dimethyldiphenoquinone, p-rosolic acid (aurin), 2,6-di-tert-butyl-4-benzylidenebenzoquinone, 2,5-di-tert-amylhydroquinone.

N-Oxyls may, for example, be 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, 4,4',4''-tris(2,2,6,6-tetramethylpiperidinyloxy) phosphite, 3-oxo-2,2,5,5-tetramethylpyrrolidine N-oxyl, 1-oxyl-2,2,6,6-tetramethyl-4-methoxypiperidine, 1-oxyl-2,2,6,6-tetramethyl-4-trimethylsilyloxypiperidine, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl (4-tert-butyl)benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethyl-4-piperidinyl) 1,10-decanedioate, bis(1-oxyl-2,2,6,6-tetramethyl-4-piperidinyl) n-butylmalonate, bis(1-oxyl-2,2,6,6-tetramethyl-4-piperidinyl) phthalate, bis(1-oxyl-2,2,6,6-tetramethyl-4-piperidinyl) isophthalate, bis(1-oxyl-2,2,6,6-tetramethyl-4-piperidinyl)terephthalate, bis(1-oxyl-2,2,6,6-tetramethyl-4-piperidinyl) hexahydroterephthalate, N,N'-bis(1-oxyl-2,2,6,6-tetramethyl-4-piperidinyl)adipamide, N-(1-oxyl-2,2,6,6-tetramethyl-4-piperidinyl)caprolactam, N-(1-oxyl-2,2,6,6-tetramethyl-4-piperidinyl)dodecylsuccinimide, 2,4,6-tris[N-butyl-N-(1-oxyl-2,2,6,6-tetramethyl-4-piperidinyl]triazine, N,N'-bis(1-oxyl-2,2,6,6-tetramethyl-4-piperidinyl)-N,N'-bisformyl-1,6-diaminohexane, or 4,4'-ethylenebis(1-oxyl-2,2,6,6-tetramethyl-3-piperazinone). The corresponding products which, as experience has shown, can form as a result of at least partial disproportionation in acidic media likewise form part of the subject-matter of the invention.

Aromatic amines or phenylenediamines may, for example, be N,N-diphenylamine, N-nitrosodiphenylamine, nitrosodiethylaniline, N,N'-dialkyl-para-phenylenediamine, wherein the alkyl radicals can be the same or different and may each independently contain from 1 to 4 carbon atoms and be straight-chain or branched, for example N,N'-di-iso-butyl-p-phenylenediamine, N,N'-di-iso-propyl-p-phenylenediamine, Irganox 5057 from Ciba Spezialitätenchemie, N,N'-di-iso-butyl-p-phenylenediamine, N,N'-di-iso-propyl-p-phenylenediamine, p-phenylenediamine, N-phenyl-p-phenylenediamine, N,N'-diphenyl-p-phenylenediamine, N-isopropyl-N-phenyl-p-phenylenediamine, N,N'-di-sec-butyl-p-phenylenediamine (Kerobit® BPD from BASF AG), N-phenyl-N'-isopropyl-p-phenylenediamine (Vulkanox® 4010 from Bayer AG), N-(1,3-dimethylbutyl)-N'-phenyl-p-phenylenediamine, N-phenyl-2-naphthylamine, iminodibenzyl, N,N'-diphenylbenzidine, N-phenyltetraaniline, acridone, 3-hydroxydiphenylamine or 4-hydroxydiphenylamine.

Hydroxylamines may, for example, be N,N-diethylhydroxylamine or N,N-dibenzylhydroxylamine.

Urea derivatives may, for example, be urea or thiourea.

Sulfonamides effective as stabilizer are described, for example, in the German patent application having an earlier priority date and the reference number 10204280.2.

The stabilizers used in the process according to the invention are preferably compounds selected from the group consisting of sulfur compounds, N-oxyls, phenols, hydroquinones and derivatives of ethylenediamines such as ethylenediamine or diethylenetriamines.

The stabilizers used in the process according to the invention are more preferably 4-hydroxy-2,2,6,6-tetramethylpiperidin-1-yloxy (HO-TEMPO), 4-methoxy-2,2,6,6-tetramethylpiperidin-1-yloxy (MeO-TEMPO), phenothiazine, diethylhydroxylamine (DEHA) or N,N'-di-sec-butyl-p-phenylenediamine (Kerobit® BPD) or mixtures of two or more of these compounds.

In the process according to the invention, the stabilizers are used in an amount of generally from 1 to 500 ppm, based on the overall reaction solution, preferably from 10 to 400 ppm, more preferably from 20 to 300 ppm.

In addition to the catalyst and at least one stabilizer, the process according to the invention may also be carried out in the presence of at least one costabilizer.

The costabilizers used in the process according to the invention may be compounds of the general formula IV.

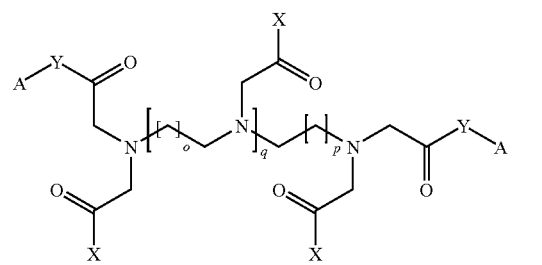

IV where o, p, q, X, Y and A are each defined as follows:

X is in each case independently selected from the group consisting of OH, $NH_2$, $OR^5$, $NHR^5$, where $R^5$ is selected from the group consisting of $C_1$-$C_{10}$-alkyl, $C_2$-$C_{10}$-alkenyl, $C_2$-$C_{10}$-alkynyl, $C_3$-$C_{10}$-cycloalkyl, $C_7$-$C_{18}$-aralkyl, $C_6$-$C_{18}$-aryl, N-alkyl and O-polyol, preferably N-alkyl or O-polyol, Y is in each case independently an atom or atomic moiety selected from O and NH, A is in each case independently a radical selected from the group consisting of saturated or unsaturated, linear or branched $C_4$-$C_{20}$ radical, optionally substituted with a functional group selected from the group consisting of the hydroxyl, aldehyde, keto, amino, amido, imido, imino, ether, thioether, carboxyl group and derivatives thereof, and halogens, phosphines and phosphites,

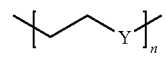

where n in each case independently has an average value of from 1 to 15, o, p in each case independently have an average value of from 0 to 5, q is 0 or 1.

According to the invention, average value means that n, o and p may also assume fractional values when there is a nonuniform mixture of compounds of the general formulae V, VI or VII in which n, o or p in the individual molecules have different values. In that case, the average values for n, o and p are the averages averaged over all compounds present. An average value of n equals 0.5 means, for example, that n is 1 in half of the compounds and n is 0 in the other half.

Particular preference is given to o, p, q, X, Y and A in the compound of the general formula IV being defined as follows:

X is in each case independently a radical selected from OH and $NH_2$,

Y is in each case independently an atom or atomic moiety selected from O and NH, A is in each case independently a radical selected from the group consisting of saturated or unsaturated, linearer or branched $C_4$-$C_{14}$ radical,

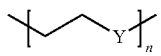

where n in each case independently has an average value of from 1 to 14, o, p are in each case independently an integer of from 0 to 3, q is 0 or 1.

Very particular preference is given to using the compounds V, VI and/or VII as costabilizers in the process according to the invention.

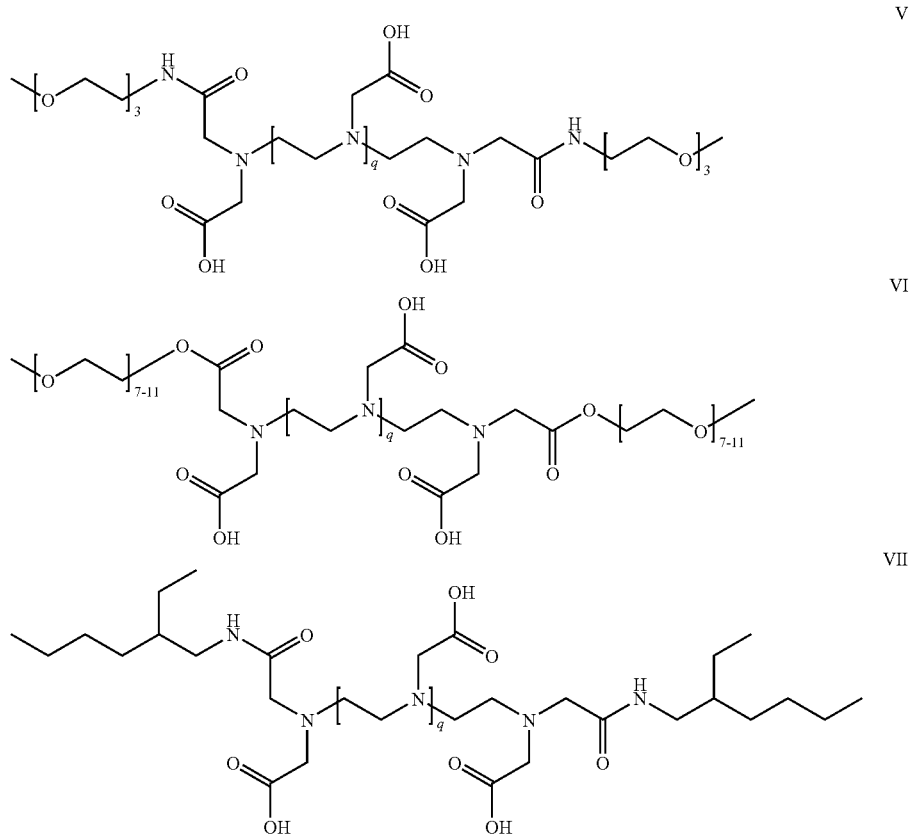

In the compounds of the formula V, VI and/or VII which are used with very particular preference, q is 0 or 1.

In process according to the invention, the stabilizers are used in an amount of from 2 to 300 ppm, based on the overall reaction solution, preferably from 10 to 250 ppm, more preferably from 20 to 200 ppm.

The process according to the invention is preferably carried out in the liquid phase. It is possible in accordance with the invention to use the NH compound itself which is to be converted in the reaction as the solvent. It is also possible to use suitable other solvents. Suitable solvents are notable in that both the NH compound and the catalyst dissolve in them, they do not react chemically with the compounds used, i.e. they in particular do not have any acidic sites which would scavenge the basic groups, and they can be removed again from the system after the synthesis of the N-alkenyl compounds readily, preferably by distillation.

Examples of suitable solvents for the process according to the invention are N-methylpyrrolidone, tetrahydrofuran or dialkyl ethers of glycols, di-, oligo- or polyglycols, and mixtures thereof.

The process according to the invention can be carried out, for example, as follows:

In the first step of the process according to the invention, the catalyst is contacted with the NH compound. It is possible that, the catalyst is added as a solid to the NH compound or to a solution of the NH compound in a suitable solvent. It is likewise possible in accordance with the invention to add a solution or dispersion of the catalyst to the NH compound.

The catalyst may be dissolved or dispersed in a suitable solvent, for example water, alcohol or the appropriate NH compound.

The catalyst is preferably added by dissolving the solid in the appropriate liquid NH compound, or by adding a solution or dispersion of the catalyst in the NH compound. It is also possible to dilute the NH compound or the solution or dispersion of the catalyst in the NH compound with a suitable solvent.

When potassium hydride is used as the catalyst, it is preferably added as a solid or dissolved or dispersed in an inert, i.e. anhydrous, solvent which does not react with the potassium hydride.

The solution or dispersion of the catalyst in the appropriate NH compound or solutions thereof is prepared generally by the customary processes, by contacting the solid catalyst with the liquid with intensive mixing. This achieves accelerated dissolution or dispersion of the solid and counteracts localized overheating as a result of the heat of dissolution. Suitable apparatus is known to those skilled in the art. Without limitation, stirred tanks are one example. The liquid is initially charged and the solid catalyst is metered in continuously or in portions with intensive mixing, if appropriate over a period of time.

When the catalysts used in the process according to the invention are hydroxides or alkoxides as alkali metal compounds, water or alcohols are formed as liquid by-products in the reaction of the NH compound with the alkali metal compounds in an equilibrium reaction. A selective removal of the water of reaction formed and/or of the alcohol of reaction formed achieves shifting of the equilibrium in the direction of the alkali metal salt of the NH compound, so that the salt stage mentioned is obtained in sufficient concentration.

When hydrides are used as the alkali metal compound, the salt of the NH compound and gaseous hydrogen as a by-product are formed in the reaction with the appropriate NH compound. In this case, the hydrogen escapes from the reaction mixture in gaseous form and can be removed by passing, for example, nitrogen through, so that the salt stage mentioned is likewise formed in this way. Suitable methods for removing the hydrogen formed are known to those skilled in the art.

The alkali metal compound can be added to the NH compound in a separate process step before and also, if appropriate, during the removal of the water or alcohol of reaction. The advantageous removal of any water and/or alcohol of reaction formed contributes to the achievement of a particularly high selectivity and yield of N-alkenyl compounds.

Particularly preferred methods for removing the water of reaction or the low molecular weight alcohols of reaction are evaporation, binding to a suitable desiccant (adsorption) and discharge through a suitable membrane. The methods mentioned may also be employed when an aqueous or alcoholic catalyst solution is used.

Preference is given to evaporating the water or the alcohol of reaction at elevated temperature between 50 and 150° C. and a reduced pressure of from 1 mbar to atmospheric pressure.

The evaporation may be effected in various ways. For example, it can be effected in a mixed vessel (for example stirred tank) by heating and/or applying a reduced pressure. It is also possible to strip out by passing an inert gas, for example nitrogen, through. The evaporation may also be effected when the solutions are passed through an evaporator. Suitable units are described in the relevant technical literature (see, for example, Ullmann's Encyclopedia of Industrial Chemistry, $6^{th}$ Edition, 1998 Electronic Release, Chapter "Evaporation").

A particularly preferred evaporation process is distillation. It may be carried out batchwise, semicontinuously or continuously. In the batchwise distillation, the NH compound and the catalyst which may be fully or else only partially dissolved are initially charged in the distillation phase and the water of reaction or the alcohol of reaction are distilled off by increasing the temperature and/or lowering the pressure. In the semicontinuous distillation, for example, a solution of the catalyst in the NH compound is fed to the column section and the water of reaction or the alcohol of reaction are distilled off continuously. The anhydrous or alcohol-free product collects in the distillation still. The continuous distillation differs from the semicontinuous distillation mainly in that the anhydrous or alcohol-free product is removed continuously from the bottom. The distillations are preferably carried out at a pressure of <1 bar.

When a desiccant is used, the exothermic adsorption of small molecules on suitable high-surface area solids is utilized. Particular emphasis should be given in this context to the removal of water. The technical literature describes a multitude of suitable desiccants (see, for example, Ullmann's Encyclopedia of Industrial Chemistry, $6^{th}$ Edition, 1998, Electronic Release, Chapter "Zeolites"). The drying may also proceed by various procedures. In one variant, for example, the desiccant is disposed directly in the reaction system in which the later reaction with the alkyne is effected. In another variant, the solution is passed through a bed of the desiccant and only subsequently introduced in the alkenylation reactor.

The water of reaction and/or the alcohol of reaction may if appropriate also be carried out by crystallization, preferably at temperatures below 0° C.

The water of reaction and/or the alcohol of reaction are removed preferably by the above-discussed methods of evaporation and/or adsorption. It is also possible to combine the two methods and this is in some cases even advantageous. Preference is further given to the removal of the water of reaction by crystallization.

In the removal of the water of reaction or of the alcohol of reaction, it is advantageous when a residual content of water or alcohol of <1% by weight, preferably <0.5% by weight, more preferably <0.2% by weight, based in each case on the total amount of liquid, is attained.

The stabilizer and, where present, the costabilizer can in principle be added in the process according to the invention at any possible time. For instance, it is possible first to add the stabilizer and, where present, the costabilizer before the catalyst is added to the NH compound or to the solution of the NH compound in a suitable solvent. It is also possible to add the stabilizer and, where present, the costabilizer after addition of the catalyst, but before removal of the water or alcohol of reaction. It is also possible in accordance with the invention to add the stabilizer and, where present, the costabilizer after the removal of the water of reaction or alcohol of reaction. In this case, it has to be ensured that the stabilizer added and, where present, the costabilizer are free of water.

Preference is given to adding the stabilizer and, where present, the costabilizer after the catalyst has been added and after the water or alcohol of reaction has been removed.

When the stabilizer and, where present, the costabilizer comprise water or low molecular weight monoalcohols, these have to be removed before addition. However, preference is given in this case to adding the stabilizer and, where present, the costabilizer to the NH compound/catalyst solution before the process stage for removing the water of reaction or the alcohol of reaction.

The reaction with the alkyne is effected by contacting the above-described solution which comprises the NH compound, the catalyst and the stabilizer and, where present, the costabilizer and has been worked up (i.e. is anhydrous and/or alcohol free) with the alkyne in the liquid phase. The inventive NH compound/catalyst/stabilizer solution may nevertheless be diluted by an anhydrous and monoalcohol-free solvent. Suitable solvents are generally all of those which can also be used in the dissolution of the NH compound and of the catalysts. Examples of suitable solvents are N-methylpyrrolidone, tetrahydrofuran or dialkyl ethers of glycols, di-, oligo- or polyglycols. Preference is given to carrying out the reaction undiluted, i.e. without addition of a further solvent.

The reaction with the alkyne may be effected in various ways. In the semicontinuous process, all of the NH compound/catalyst/stabilizer solution is initially charged and the alkyne is metered in according to the reaction profile. The product solution is normally removed only after completion of the reaction.

In the continuous process, the NH compound/catalyst/stabilizer solution and the alkyne are fed in continuously and the corresponding product solution is removed continuously.

According to the invention, NH compound/catalyst/stabilizer solution refers to a solution which may, if appropriate, also comprise a costabilizer.

The inventive reaction is carried out generally at a temperature of 80 to 240° C., preferably of from 100 to 200° C., more preferably of from 130 to 180° C.

The inventive reaction is generally carried out at a pressure of the alkyne of <50 bar, preferably of <30 bar, most preferably of <24 bar. However, the overall pressure of the system may be distinctly higher, since the blanketing gas atmosphere may, for example, also comprise inert gases such as nitrogen or noble gases which can be introduced by controlled injection. Thus, an overall pressure in the system of, for example, 200 bar is possible immediately.

When high molecular weight alkynes are used, the pressure of the alkyne which is established is very low and may, for example, be below 1 bar. In the case of the low molecular weight alkynes, for instance acetylene, propyne and 1-butyne, a pressure of the alkyne of >1 bar is generally set. This achieves a more economic space-time yield.

When the alkyne used in the alkenylation is acetylene, it is preferably carried out at an acetylene pressure of from 5 to 30 bar, more preferably of from 8 to 24 bar and most preferably of from 16 to 20 bar.

Useful reactors for the inventive alkenylation are in principle the apparatus, described in the relevant technical literature, for gas-liquid reactions. To achieve a high space-time yield, intensive mixing between the NH compound/catalyst/stabilizer solution and the alkyne is important. Nonlimiting examples include stirred tanks, stirred tank batteries, flow tubes (preferably having internals), bubble columns and loop reactors.

The reaction effluent is worked up by known methods. Preference is given to a distillation into several fractions. The distillation is carried out preferably at a pressure of <1 bar. The distillation may be carried out batchwise, semicontinuously or continuously. In addition, it may be carried out in a column, if appropriate having side drawers, or else in a plurality of columns connected in series. Suitable processes are known to those skilled in the art.

N-Alkenyl compounds may be obtained by the process according to the invention, as described, in a simple manner with a purity of >99.8%.

Any unconverted NH compound which has been removed may be recycled without further purification measures in the process according to the invention. For this purpose, it is not necessary to recover the feedstock in high purity, so that it is possible to use a crudely distilled fraction. However, it is advantageous to remove the distinctly higher-boiling products.

In a general embodiment of the process according to the invention, the basic alkali metal compound (catalyst) is introduced into the liquid NH compound which has if appropriate been diluted or dissolved with solvent, and mixed. The resulting solution is then incipiently distilled and fed to a stirred tank. The distillation removes the water of reaction or the alcohol of reaction. The stabilizer and, where present, the costabilizer are introduced into the now virtually anhydrous and alcohol-free solution. At a temperature of from 80 to 240° C., the alkyne is now introduced with intensive mixing. In the case of the preferred use of acetylene, preference is given to introducing it up to a pressure of 24 bar. Alkyne which has been consumed is replenished. On completion of the absorption of the alkyne, the reaction system is decompressed. The reaction solution is transferred into a distillation column and the N-alkenyl compound, after the lower-boiling components had been removed overhead, is isolated in high purity.

In a further general embodiment, a virtually concentrated solution, i.e. about 80% of the maximum solubility of the basic alkali metal compound in the NH compound, is prepared in a mixing vessel. It is also possible to add a from 30 to 70% by weight solution of the alkali metal compound in water to the NH compound. This solution is fed continuously to a vacuum distillation column and the water of reaction formed is drawn off overhead. The anhydrous catalyst/NH compound solution is removed continuously from the bottom and admixed with further, anhydrous NH compound and with anhydrous stabilizer and, where present, costabilizer. At this point, the recycle streams are also fed in. The reactant mixture is now fed to a continuous loop reactor. There, the reaction with the alkyne is effected at a temperature of from 80 to 240° C. In the case of the preferred use of acetylene, preference is given to introducing it up to a pressure of 24 bar. The reaction solution is withdrawn continuously from the loop reactor and worked up by distillation. The N-alkenyl compound is isolated as a pure product. Recovered, unconverted NH compound is recycled.

The process according to the invention enables a simple preparation of N-alkenyl compounds by reacting the corresponding NH compounds with alkynes in the presence of catalysts and stabilizers in very high yield and purity.

In addition, the present invention also relates to the use of stabilizers for increasing the selectivity in a process for preparing N-alkenyl compounds by reacting the corresponding NH compounds with alkynes in the liquid phase in the presence of a catalyst, and the stabilizers, the N-alkenyl compounds, the NH compounds, the alkynes, the catalysts and the process parameters are specified in the above section of the description.

In particular, the present invention relates to the use of stabilizers in the process according to the invention.

EXAMPLES

Experiment to Assess the Stabilizing Properties

In a 100 ml round-bottom flask, a mixture of N-vinylpyrrolidone (50% by weight) and 2-pyrrolidone (50% by weight) is admixed with a small amount of potassium hydride and the stabilizer system to be investigated, and stirred until the solution is homogeneous. Subsequently, the resulting mixture is heated to 150° C. and samples are taken at intervals of 15-30 minutes. These samples are analyzed for the content of polyvinylpyrrolidone.

Results

The table which follows illustrates the results

| Stabilizer | Costabilizer | Amount of stabilizer [ppm] | Amount of costabilizer [ppm] | Polymer content up to 60 min [% by wt.] | Polymer content up to 180 min [% by wt.] |
|---|---|---|---|---|---|
| None | None | | | 31.2 | 43.0 |
| HO-TEMPO | None | 100 | | 0.1 | 32.9 |

-continued

| Stabilizer | Costabilizer | Amount of stabilizer [ppm] | Amount of costabilizer [ppm] | Polymer content up to 60 min [% by wt.] | Polymer content up to 180 min [% by wt.] |
|---|---|---|---|---|---|
| MeO-TEMPO | None | 100 | | 0.85 | 25.7 |
| Phenothiazine (PTZ) | None | 100 | | 0.1 | 0.1 |
| Phenothiazine (PTZ) | VII | 20 | 20 | 2.25 | 4.7 |
| Diethylhydroxylamine (DEHA) | None | 100 | | 1.17 | 2.26 |
| Kerobit® BPD | None | 100 | | 1.47 | 2.98 |

The identified compounds are subsequently investigated in a vinylation apparatus for the selectivity-improving properties.

The experimental apparatus comprises a reservoir from which the catalyst solution is metered into a pumped circulation system with trace heating. The pyrrolidone is initially incipiently distilled outside the plant with KOH or KOMe, i.e. the catalyst is generated by distilling off water or methanol in pyrrolidone. The temperature-controlled pumped circulation system is maintained by a reaction mixing pump, which dissolves acetylene into the reaction mixture. The acetylene is metered by a Combi-Flow instrument at an initial pressure between 23 and 25 bar. The mass flow rate in the mixing circuit is large in comparison to the amount metered, so that the plant can be operated like a stirred autoclave. At the branch of the mixing circuit, samples are taken. Connected downstream of the mixing circuit is an effluent vessel. The content of the samples is determined with calibrated gas chromatography.

The experiments are carried out at a temperature of 150° C. and a catalyst concentration of 2% (calculated as KOH). 90-91 g/h of catalyst solution and 11.7 l/h of acetylene are metered in. The pressure is 18 bar. The circulation rate in the mixing circuit is 20 kg/h; the mixing circuit volume is 72 ml. The stabilizers/costabilizers are added after the preparation of the catalyst solution.

P=pyrrolidone
VP=N-vinylpyrrolidone
A=acetylene

Calculation of pyrrolidone conversion:

$((([mol/h]P_{in}-[mol/h]P_{out})/[mol/h]P_{in})*100$

Calculation of selectivity based on pyrrolidone:

$([mol/h]VP/([mol/h]P_{in}-[mol/h]P_{out}))*100$

Calculation of selectivity based on acetylene:

$([mol/h]VP/[mol/h]A_{in})*100$

| Stabilizer | P conversion [%] | P selectivity [%] | A selectivity [%] |
|---|---|---|---|
| None | 51 | 88 | 95 |
| Phenothiazine, 100 ppm | 52 | 88 | 95 |
| Hydroxy-TEMPO, 100 ppm | 51.8 | 94.7 | 96.6 |
| Phenothiazine + comp. VI, each 50 ppm | 51 | 93 | 97 |
| Kerobit® BPT, 100 ppm | 50.9 | 92.9 | 97.08 |
| Dimethylhydroquinone, 100 ppm | 50.8 | 92.8 | 96.7 |

What is claimed is:

1. A process for preparing N-alkenyl compounds of general formula III by reacting alkynes of general formula I with NH compounds of general formula II

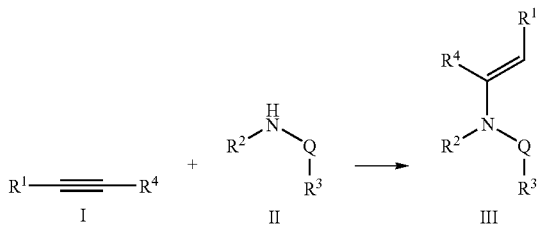

where the Q, $R^1$, $R^2$, $R^3$ and $R^4$ radicals are each defined as follows:

Q is C=O or $CR^1$ $R^1$, $R^4$ are each independently hydrogen, $C_1$-$C_{20}$-alkyl, $C_2$-$C_{20}$-alkenyl;

$R^2$, $R^3$ are each independently hydrogen, $C_1$-$C_{20}$-alkyl, $C_2$-$C_{20}$-alkenyl; or the $R^2$—N-Q-$R^3$ moiety is part of a saturated, unsaturated or aromatic, heterocyclic four- to eight-membered ring;

in the liquid phase in the presence of a catalyst, which comprises carrying out the reaction in the presence of at least one stabilizer, wherein the stabilizer is at least one selected from the group consisting of 4-hydroxy-2,2,6,6-tetramethylpiperidin-1-yloxy, 4-methoxy-2,2,6,6-tetramethylpiperidin-1-yloxy, phenothiazine, diethylhydroxylamine and N,N'-di-sec-butyl-p-phenylenediamine.

2. The process according to claim 1, wherein the catalyst used is a compound selected from the group consisting of alkali metals, alkali metal compounds, alkaline earth metal compounds, rare earth metal compounds and compounds of the metals of the platinum group or mixtures thereof.

3. The process according to claim 1, wherein the catalyst is present in a molar proportion of from 0.05 to 10 mol % based on the molar amount of the NH compound used.

4. The process according to claim 1, wherein the reaction is carried out at a temperature of from 80 to 240° C.

5. The process according to claim 1, wherein the reaction is carried out at a pressure of the alkyne of <50 bar.

6. The process according to claim 1, which is carried out in the presence of at least one costabilizer.

7. The process according to claim 6, wherein the costabilizer is a compound of formula IV

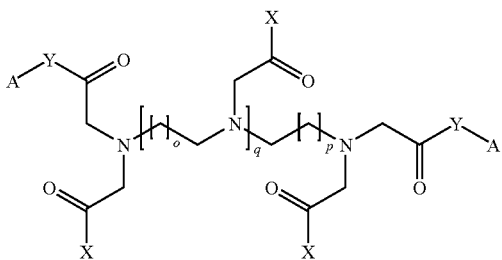

where o, p, q, X, Y and A are each defined as follows:
  X is in each case independently selected from the group consisting of OH, $NH_2$, $OR^5$, $NHR^5$, where $R^5$ is selected from the group consisting of $C_1$-$C_{10}$-alkyl, $C_2$-$C_{10}$-alkenyl, $C_2$-$C_{10}$-alkynyl, $C_3$-$C_{10}$-cycloalkyl, $C_7$-$C_{18}$-aralkyl, $C_6$-$C_{18}$-aryl, N-alkyl and O-polyol,
  Y is in each case independently an atom or atomic moiety selected from O and NH,
  A is in each case independently a radical selected from the group consisting of saturated or unsaturated, linear or branched $C_4$-$C_{20}$ radical, optionally substituted with a functional group selected from the group consisting of the hydroxyl, aldehyde, keto, amino, amido, imido, imino, ether, thioether, carboxyl group and derivatives thereof, and halogens, phosphines and phosphites,

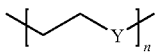

where n in each case independently has an average value of from 1 to 15,
  o, p in each case independently have an average value of from 0 to 5,
  q is 0 or 1.

8. A method of increasing the selectivity of an alkenylation reaction for preparing N-alkenyl compounds, comprising:
  reacting an NH compound of formula II with an alkyne of formula I to form an N-alkenyl compound of formula III:

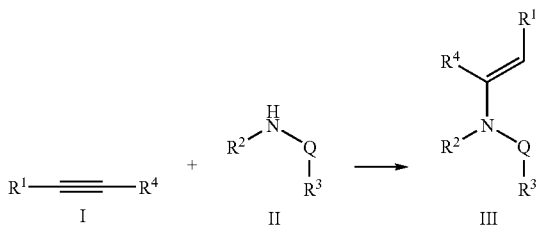

wherein Q, $R^1$, $R^2$, $R^3$ and $R^4$ are each defined as follows:
  Q is C=O or $CR^1$;
  $R^1$, $R^4$ are each independently hydrogen, $C_1$-$C_{20}$-alkyl, or $C_2$-$C_{20}$-alkenyl;
  $R^2$, $R^3$ are each independently hydrogen, $C_1$-$C_{20}$-alkyl, or $C_2$-$C_{20}$-alkenyl; or
  the $R^2$—N-Q-$R^3$ moiety is part of a saturated, unsaturated or aromatic, heterocyclic four- to eight-membered ring;
  wherein the reacting is carried out in the liquid phase in the presence of a catalyst and at least one stabilizer selected from the group consisting of 4-hydroxy-2,2,6,6-tetramethylpiperidin-1-yloxy, 4-methoxy-2,2,6,6-tetramethylpiperidin-1-yloxy, phenothiazine, diethylhydroxylamine and N,N'-di-sec-butyl-p-phenylenediamine.

9. The process of claim 1, wherein the alkyne of formula I is acetylene and the NH compound of formula II is selected from the group consisting of 2-pyrrolidone, 2-piperidone, ε-caprolactam, formamide and imidazole.

10. The process of claim 1, wherein the alkyne of formula I is acetylene.

11. The process of claim 1, wherein the NH compound of formula II is at least one selected from the group consisting of 2-pyrrolidone, 2-piperidone, ε-caprolactam, formamide and imidazole.

12. The process of claim 1, which comprises:
  reacting 2-pyrrolidone with acetylene to form N-vinyl-2-pyrrolidone.

13. The process of claim 1, which comprises:
  reacting acetylene with 2-piperidone to give N-vinyl-2-piperidone.

14. The process of claim 1, which comprises:
  reacting acetylene with ε-caprolactam to form N-vinyl-ε-caprolactam.

15. The process of claim 1, which comprises:
  reacting acetylene with formamide to form N-vinylformamide.

16. The process of claim 1, which comprises:
  reacting acetylene with imidazole to form N-vinylimidazole.

17. The process of claim 1, wherein
  Q is C=O or $CR^1$;
  $R^1$, $R^4$ are each independently hydrogen, $C_1$-$C_{20}$-alkyl, or $C_2$-$C_{20}$-alkenyl; and
  $R^2$, $R^3$ are each independently hydrogen, $C_1$-$C_{20}$-alkyl, or $C_2$-$C_{20}$-alkenyl.

* * * * *